(12) United States Patent
Amtmann et al.

(10) Patent No.: US 6,347,277 B2
(45) Date of Patent: Feb. 12, 2002

(54) METHOD AND DEVICE FOR CALIBRATING A PROBE SYSTEM

(75) Inventors: Markus Amtmann, Regensburg; Stephan Bolz, Pfatter; Jürgen Rössler, Münnerstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/781,673

(22) Filed: Feb. 12, 2001

Related U.S. Application Data

(63) Continuation of application No. PCT/DE99/02490, filed on Aug. 10, 1999.

(30) Foreign Application Priority Data

Aug. 10, 1998 (DE) ............................................ 198 36 127

(51) Int. Cl.$^7$ ...................... G01N 27/419; F02D 41/14; G06F 19/00
(52) U.S. Cl. ...................... 701/114; 701/114; 73/23.32; 204/406; 204/424
(58) Field of Search ................................ 123/693, 694, 123/696; 701/109, 114, 115; 73/23.31, 23.32; 204/400, 406, 424, 425, 426

(56) References Cited

U.S. PATENT DOCUMENTS

| 4,214,308 A | | 7/1980 | Carp ........................... 701/114 |
| 4,944,274 A | * | 7/1990 | Itsuji et al. .................. 123/693 |
| 5,231,864 A | * | 8/1993 | Ishida et al. ................ 73/23.32 |
| 6,149,786 A | * | 11/2000 | Patrick et al. .............. 204/406 |
| 6,227,033 B1 | * | 5/2001 | Kainz ......................... 73/23.32 |
| 6,254,750 B1 | * | 7/2001 | Patrick et al. .............. 204/425 |

FOREIGN PATENT DOCUMENTS

EP   0 507 149 A1   10/1992

OTHER PUBLICATIONS

"Performance of Thick Film NO$_x$ Sensor on Diesel and Gasoline Engines"(Kato et al.), dated 1997, XP–002127410, pp. 1246–1253, as mentioned on p. 2 of the specification.

* cited by examiner

*Primary Examiner*—Willis R. Wolfe
(74) *Attorney, Agent, or Firm*—Herbert L. Lerner; Laurence A. Greenberg; Werner H. Stemer

(57) ABSTRACT

A control circuit of an exhaust probe has a microcontroller and an analog circuitry. Measured values which are recorded in a test chamber under predefined test conditions are stored in characteristic maps in a programmable read-only memory. These values are then used as a reference for a subsequent recalibration of a probe system.

17 Claims, 3 Drawing Sheets

METHOD AND DEVICE FOR CALIBRATING A PROBE SYSTEM

CROSS-REFERENCE TO RELATED APPLICATION

This application is a continuation of copending International Application No. PCT/DE99/02490, filed Aug. 10, 1999, which designated the United States.

BACKGROUND OF THE INVENTION

Field of the Invention

The invention relates to a method and a device for calibrating a probe system including an exhaust probe and a control circuit for a motor vehicle.

As environmental awareness is increasing and resulting exhaust gas regulations are becoming increasingly strict, the need to reduce pollutants in exhaust gases of internal combustion engines in motor vehicles is becoming increasingly important. Compliance with the currently valid emission limits for pollutants such as carbon monoxide (CO), nitrogen oxide ($NO_x$) and hydrocarbons (HC) requires selective engine control on the one hand and catalytic post-treatment of the exhaust gases on the other. For both measures it is necessary to get measurement values with exhaust gas probes—for example lambda probes or $NO_x$ probes. The term probe will be used below to mean a unit formed of a sensor, a sensor line and a sensor plug.

It is known to use thick-film sensors to measure the concentration of pollutants in the exhaust gas of an internal combustion engine. Such a sensor is described, using the example of an $NO_x$ sensor, by N. Kato et al., in the publication "Performance of Thick Film $NO_x$ Sensor on Diesel and Gasoline Engines" Society of Automotive Engineers, publication 970858, 1997. This $NO_x$ sensor has two measuring cells and three oxygen pumping cells and implements the following measuring concept: in a first measuring cell to which the gas which is to be measured is fed via a diffusion barrier, a first oxygen concentration is set through the use of a first oxygen ion pump current, no decomposition of $NO_x$ taking place. In a second measuring cell, which is connected to the first measuring cell via a diffusion barrier, the oxygen content is reduced further through the use of a second oxygen ion pump current and $NO_x$ is decomposed at a measuring electrode. The oxygen which is generated in this way is taken as a measure of the $NO_x$ concentration. The entire $NO_x$ sensor is heated to a higher temperature, for example 700° C., through the use of an electric heating element.

When such sensors are manufactured, large fabrication tolerances occur for technological reasons. In addition, the properties of the sensor, for example the impedance of the pump cells, change over time. Because the signal currents of exhaust probes with such sensors are usually only in the nA range, the component tolerances of the control circuit also influence the accuracy or precision of the measurement to a considerable degree. A measuring precision which is sufficient for a mass produced component in a motor vehicle can thus be ensured only through the use of individual standardization of the probe control circuit system—referred to below as probe system—and, in addition, a recalibration must be possible during the service life of the probe.

SUMMARY OF THE INVENTION

It is accordingly an object of the invention to provide a method for calibrating a probe system which overcomes the above-mentioned disadvantages of the heretofore-known methods of this general type and which makes it possible to perform an individual calibration on exhaust probes, together with the associated control circuit, at the end of the manufacturing process and in the course of the service life of such exhaust probes, and which allows to compensate the component tolerances of the control circuit.

With the foregoing and other objects in view there is provided, in accordance with the invention, a method for calibrating a probe system, the method includes the steps of:

providing a probe system including an exhaust probe and a control circuit with a microcontroller and an analog circuitry, the exhaust probe operating according a principle of a galvanic oxygen concentration cell with a solid electrolyte;

using the microcontroller in conjunction with the analog circuitry for controlling pump currents;

acquiring measured values with the exhaust probe under given test conditions;

reading the measured values into the microcontroller; and storing the measured values read into the microcontroller in a programmable read-only memory provided in the control circuit as correction values or test values.

According to an alternative embodiment of the invention, there is provided a method for calibrating a probe system, which includes the steps of:

providing a probe system including an exhaust probe and a control circuit with a microcontroller and an analog circuitry, the exhaust probe operating according a principle of a galvanic oxygen concentration cell with a solid electrolyte;

using the microcontroller in conjunction with the analog circuitry for controlling pump currents;

acquiring measured values with the exhaust probe under given test conditions;

reading the measured values into the microcontroller;

evaluating the measured values in the microcontroller for providing evaluated measured values; and storing the evaluated measured values in a programmable read-only memory provided in the control circuit as correction values or test values.

According to another mode of the invention, the correction values or test values are stored in characteristic maps in the programmable read-only memory.

According to yet another mode of the invention, the programmable read-only memory is provided as an integrated programmable read-only memory integrated into the microcontroller.

According to a further mode of the invention, the measured values of the exhaust probe are acquired under electrically neutral conditions, and the measured values recorded under the electrically neutral conditions are stored as the correction values in the programmable read-only memory.

According to another mode of the invention, the pump currents are corrected with the correction values.

According to yet another mode of the invention, the test values are used as a reference for a subsequent recalibration of the probe system.

With the objects of the invention in view there is also provided, a device for calibrating a sensor system, including:

an exhaust probe including a test chamber to be provided with a test gas with variable test parameters;

a control circuit connected to the exhaust probe;

a test control computer for setting and monitoring the variable test parameters in the test chamber; and a data line, the control circuit and the test control computer communicating with one another via the data line.

According to another feature of the invention, the control circuit has a serial interface, and the serial interface connects the data line to the control circuit.

According to yet another feature of the invention, the exhaust probe is a motor vehicle exhaust probe.

According to another feature of the invention, the exhaust probe operates according a principle of a galvanic oxygen concentration cell with a solid electrolyte, and the exhaust probe acquires measured values under given test conditions, and the control circuit controls pump currents for the exhaust probe, and the control circuit stores the measured values as correction values or test values.

According to a further feature of the invention, the control circuit corrects the pump currents based on the measured values.

If a microcontroller in conjunction with analog circuitry is used to control the pump currents, it is possible to store application-specific data of the probe system. The measured values which are recorded under predefined test conditions are stored as correction or test values in a programmable read-only memory (ROM), for example an EPROM (erasable programmable read-only memory), which is preferably integrated into the microcontroller. The test values are then used as a reference for independent recalibration of the probe system during its service life. The correction values are used to compensate further component tolerances, for example offset voltages of operational amplifiers.

Other features which are considered as characteristic for the invention are set forth in the appended claims.

Although the invention is illustrated and described herein as embodied in a method and device for calibrating a probe system, composed of an exhaust probe and a control circuit for a motor vehicle, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Referring now to the figures of the drawings, an exemplary embodiment of the invention is described with reference to a $NO_x$ sensor. Thick-film $NO_x$ sensors are composed of a multi-layer, sintered ceramic substrate. During the manufacturing process, a plurality of electrodes are applied to the individual ceramic carriers. These electrodes form the pump cells and measuring cells which are necessary to implement a $NO_x$ sensor. The electrical properties of the electrodes provided and of the ceramic substrate change during the sintering process and in the course of time.

Figure 1:
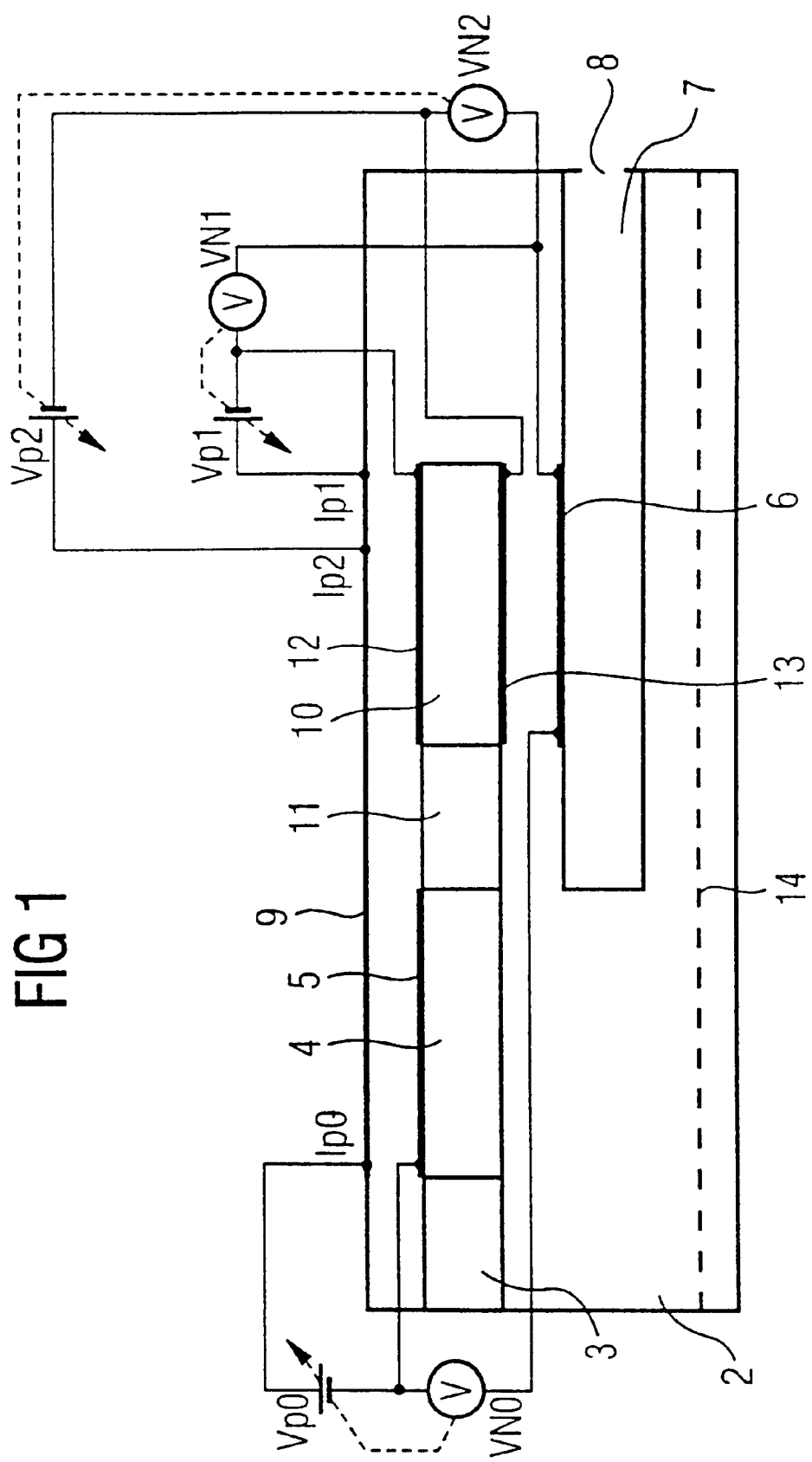
FIG. 1 is diagrammatic sectional view of a $NO_x$ sensor.

A $NO_x$ sensor 1 (FIG. 1) which is composed of a solid electrolyte 2, in this case zirconium dioxide, receives the gas which is to be measured via a first diffusion barrier 3.

The exhaust gas diffuses through the diffusion barrier 3 into a first measuring cell 4. The oxygen content in this measuring cell is measured through the use of a first Nernst voltage VN0 between a first pump electrode 5 and a reference electrode 6 which is exposed to ambient air. Here, the reference electrode is provided in an air duct 7 into which ambient air passes via an orifice 8. Both electrodes 5, 6 are conventional platinum electrodes.

According to a general method, the measured value of the first Nernst voltage VN0 is used to set a first control voltage Vp0. The control voltage Vp0 drives a first oxygen ion pump current Ip0 through the solid electrolyte 2 of the $NO_x$ sensor 1 between the first pump electrode 5 and an external electrode 9 the pump electrode s and the external electrode 9 form a first pump cell. Here, the control voltage Vp0 is set by a regulator or controller in such a way that a predefined oxygen concentration is present in the first measuring cell 4.

The first measuring cell 4 is connected to a second measuring cell 10 via a second diffusion barrier 11. The gas present in the measuring cell 4 diffuses into the second measuring cell 10 through this diffusion barrier 11. The second oxygen concentration in the second measuring cell 10 is measured through the use of a second Nernst voltage VN1 between a second pump electrode 12, which is also a platinum electrode, and the reference electrode 6, and is used by a regulator to set a second control voltage Vp1 which drives a second oxygen ion pump current Ip1. The second oxygen ion pump current Ip1 from the second measuring cell 10 flows from the second pump electrode 12 through the solid electrolyte 2 to the external electrode 9 (second pump cell). The second oxygen ion pump current Ip1 is used to set a predefined oxygen concentration in the second measuring cell 10.

The $NO_x$ concentration which is not affected by the previous procedures in the measuring cells 4 and 10 is now determined at a measuring electrode 13 which is configured so as to be catalytically active. For this purpose, a third oxygen concentration is measured through the use of a third Nernst voltage VN2 between the measuring electrode 13 and the reference electrode 6 and is used by a regulator to set a third control voltage Vp2. By applying this control voltage Vp2 between the measuring electrode 13 and the external electrode 9 (third pump cell), the $NO_x$ is decomposed and the oxygen which is released is pumped through the solid electrolyte 2 in a third oxygen ion pump current Ip2 to the external electrode 9. When there is a sufficiently low residual oxygen content in the measuring cell 10, the third oxygen ion pump current Ip2 is conducted only by oxygen ions originating from the decomposition of $NO_x$. It is thus a measure of the $NO_x$ concentration in the measuring cell 10 and thus in the exhaust gas to be measured. Because such $NO_x$ sensors have a high dependence on temperature, a heating element 14 ensures that the probe temperature is always kept in a predefined temperature range in order to maintain the necessary measuring precision.

Figure 2:
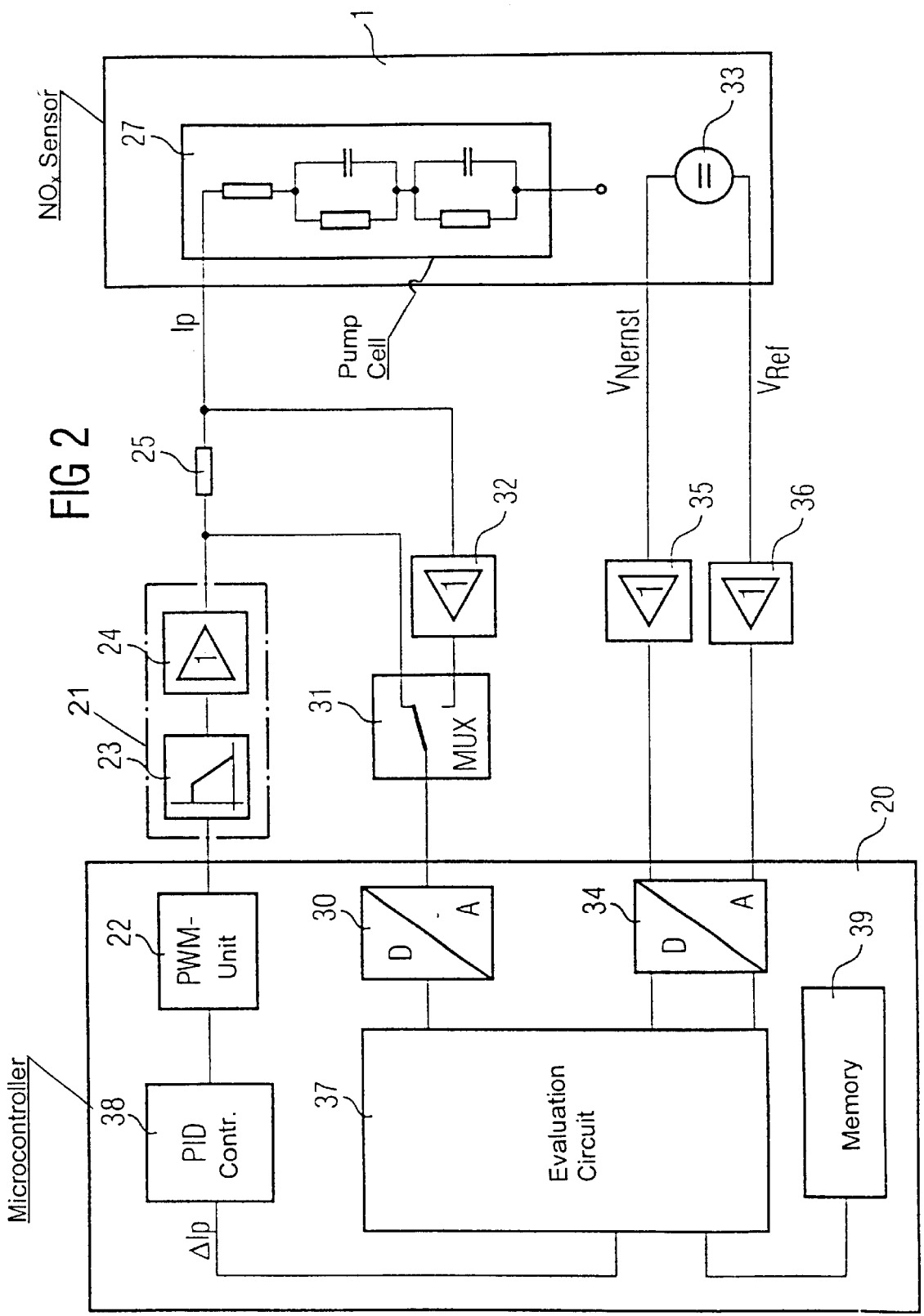
FIG. 2 is a block circuit diagram of a circuit configuration for controlling a pump current.

A microcontroller 20 in conjunction with analog circuitry 21 is used to regulate the pump currents. The circuit configuration of an individual pump current control circuit is illustrated in detail in FIG. 2. The control circuit of the entire $NO_x$ sensor has such a circuit configuration for each pump cell which is to be controlled. Here, the necessary digital circuit elements can be implemented within a single microcontroller 20. A PWM (Pulse Width Modulation) unit 22 in is the microcontroller 20 generates a pulse-width-modulated signal which is converted into a DC voltage using an analog filter circuit 23. Depending on the required current strength, this voltage is either fed directly or via an impedance transformer 24 to a measuring resistor 25 which is connected in series with the pump cell 27, to be controlled, of the $NO_x$ sensor 1. The pump cell is illustrated in FIG. 2 in the form of an equivalent circuit for the relevant impedance.

A first A/D converter 30 in the microcontroller 20 is used to input the voltage potentials alternatively upstream and downstream of the measuring resistor 25 through the use of a multiplexer 31. Because the input of the $NO_x$ sensor 1 usually has very high impedance, an impedance transformer 32, for example a buffer amplifier, can be connected into the measuring line which is used to measure the potential value downstream of the measuring resistor 25.

The Nernst voltages which are required to regulate the pump current are also calculated in the microcontroller 20. To do this, both the Nernst potential $V_{Nernst}$ and the reference potential $V_{Ref}$ of the respective measuring cell 33 of the $NO_x$ sensor 1 are input by a second A/D converter 34 in the microcontroller 20. The measuring cell 33 corresponds here either to the first measuring cell 4 or to the second measuring cell 10 in FIG. 1 and is illustrated schematically as a DC voltage source. Due to the high output impedance of the $NO_x$ sensor 1, two impedance transformers 35 and 36, for example in the form of buffer amplifiers, are also provided here.

A pump current difference $\Delta Ip$ is calculated in an evaluation circuit 37 within the microcontroller 20 from the potential values which are input and is fed to a controller 38, for example a PID controller, which controls the PWM unit 22. A programmable read-only memory 39, for example an EPROM, which is preferably integrated into the microcontroller, is used to store the potentials input at the A/D converters 30 and 34.

Figure 3:
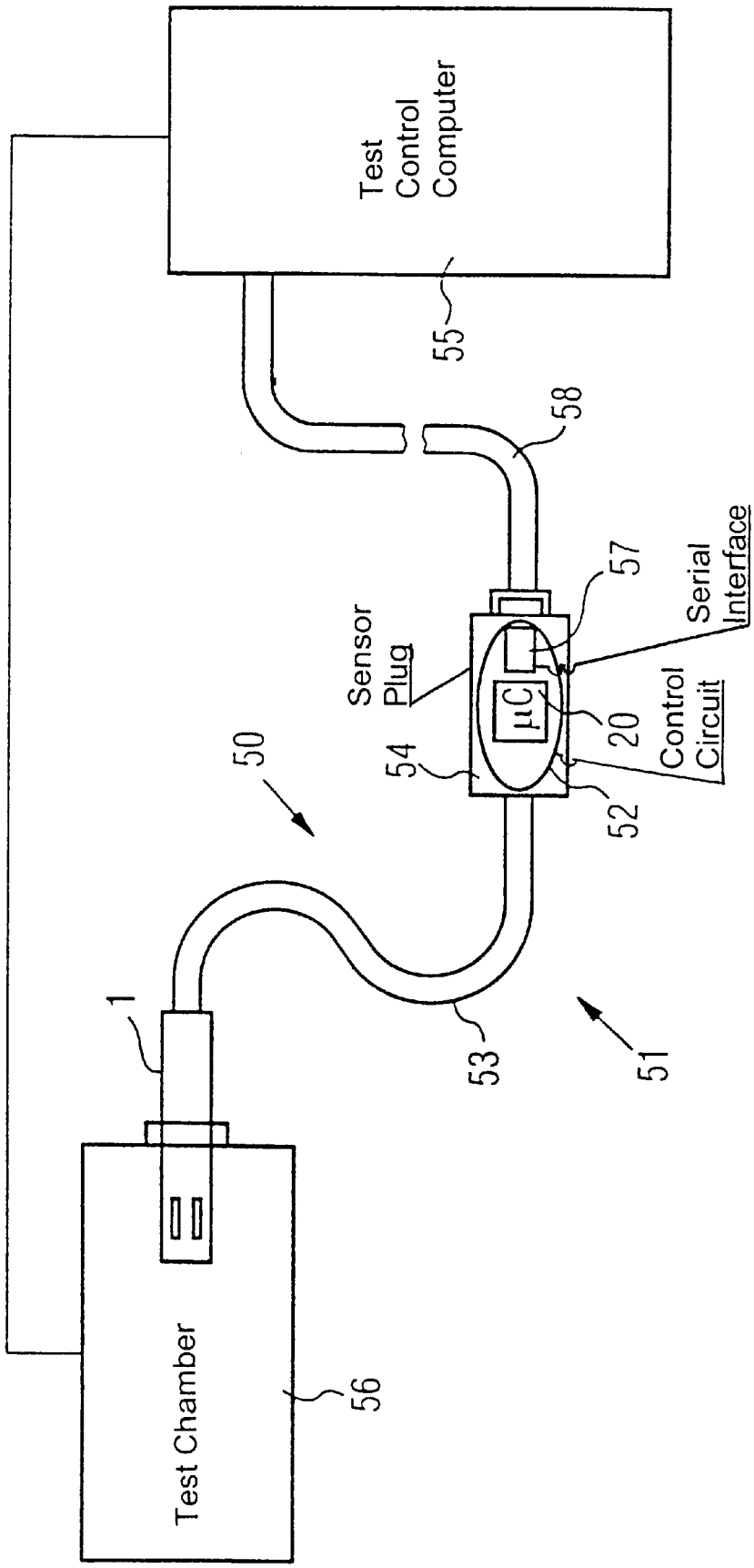
FIG. 3 is a schematic illustration of a configuration for carrying out the method according to the invention for calibrating a probe system.

A probe system 50, composed of a $NO_x$ probe 51 and the associated control circuit 52, is calibrated with the configuration according to FIG. 3. The $NO_x$ probe 51 is composed here of the $NO_x$ sensor 1, a sensor line 53 and a sensor plug 54. Providing the control circuit 52 in the housing of the sensor plug 54 results in very short connecting lines. In this way, despite the occurrence of line losses, sufficiently precise transmission of the signal currents which are usually only in the nA range can be ensured.

The test parameters, for example $NO_x$ concentration and gas temperature, are set and monitored in a test chamber 56 through the use of a test control computer 55. The $NO_x$ sensor 1 records the respective measured values and passes them on to the control circuit 52 via the sensor line 51. In the control circuit 52, the measured values which are present at the A/D converters of the microcontroller 20 are stored, either directly or after an internal evaluation, for example through the use of comparison with predefined set point values, in characteristic maps especially provided for that purpose in the programmable read-only memory 39. The communication with the test control computer 55 which is necessary to control the control circuit 52 takes place via a serial interface 57, integrated into the control circuit, and a data line 58. In order to be able to compensate fabrication tolerances and component tolerances within the control circuit which are present due to technological reasons, the individual pump current control circuits must be measured under different, characteristic operating conditions, after the probe system has been completed, that is to say after the $NO_x$ probe has been connected to the associated control circuit. In order to be able to compensate offset voltages, the probe system is initially tested under electrically neutral test conditions. To do this, the heating element is switched off and a pulse duty factor of the pulse-width-modulated signal of 0% is set, with the result that there is no longer any pump current flowing. The values which are then input by the A/D converters correspond precisely to the offset voltages present. The latter may be stored as correction values in the programmable read-only memory 39 and used to correct the respective pump currents. This compensation can also be repeated after installation of the control system in a motor vehicle, for example at the request of the central engine controller or in the course of an inspection in a workshop. Subsequently, each pump current control circuit of the probe system is successively tested under different test conditions. The pump currents which are determined during this process—i.e. the measured values present at the first A/D converter 30—are stored in the read-only memory 39 and are subsequently used as a reference for regular, independent recalibration of the system in the course of its service life. In addition, the Nernst potentials and reference potentials present at the second A/D converter 34 can also be stored in the read-only memory 39.

Using a microcontroller with integrated A/D converters allows different application-specific data of the probe system to be input and stored. In this way, any probe system can be calibrated individually and completely automatically at the end of the manufacturing process using a test device. Complex and costly tuning of electronic components, such as would be necessary with a purely analog control circuit, can thus be avoided. The possibility of independently recalibrating the probe system makes the circuit configuration of the control circuit largely independent of component tolerances.

The invention has been described by way of example for a $NO_x$ sensor, but corresponding methods and devices are also suitable for other exhaust probes which operate according to the principle of a galvanic oxygen concentration cell with a solid electrolyte, such as linear oxygen probes.

We claim:

1. A method for calibrating a probe system, the method which comprises:
   providing a probe system including an exhaust probe and a control circuit with a microcontroller and an analog circuitry, the exhaust probe operating according a principle of a galvanic oxygen concentration cell with a solid electrolyte;
   using the microcontroller in conjunction with the analog circuitry for controlling pump currents;
   acquiring measured values with the exhaust probe under given test conditions;
   reading the measured values into the microcontroller; and
   storing the measured values read into the microcontroller in a programmable read-only memory provided in the control circuit as one of correction values and test values.

2. The method according to claim 1, which comprises storing the one of the correction values and test values in characteristic maps in the programmable read-only memory.

3. The method according to claim 1, which comprises providing the programmable read-only memory as an integrated programmable read-only memory integrated into the microcontroller.

4. The method according to claim 1, which comprises:
   acquiring the measured values of the exhaust probe under electrically neutral conditions; and
   storing the measured values recorded under the electrically neutral conditions as the correction values in the programmable read-only memory.

5. The method according to claim 1, which comprises correcting the pump currents with the correction values.

6. The method according to claim 1, which comprises using the test values as a reference for a subsequent recalibration of the probe system.

7. A method for calibrating a probe system, the method which comprises:

provising a probe system including an exhaust probe and a control circuit with a microcontroller and an analog circuitry, the exhaust probe operating according a principle of a galvanic oxygen concentration cell with a solid electrolyte;

using the microcontroller in conjunction with the analog circuitry for controlling pump currents;

acquiring measured values with the exhaust probe under given test conditions;

reading the measured values into the microcontroller;

evaluating the measured values in the microcontroller for providing evaluated measured values; and storing the evaluated measured values in a programmable read-only memory provided in the control circuit as one of correction values and test values.

8. The method according to claim 7, which comprises storing the one of the correction values and test values in characteristic maps in the programmable read-only memory.

9. The method according to claim 7, which comprises providing the programmable read-only memory as an integrated programmable read-only memory integrated into the microcontroller.

10. The method according to claim 7, which comprises acquiring the measured values of the exhaust probe under electrically neutral conditions.

11. The method according to claim 7, which comprises correcting the pump currents with the correction values.

12. The method according to claim 7, which comprises using the test values as a reference for a subsequent recalibration of the probe system.

13. A device for calibrating a sensor system, comprising:

an exhaust probe including a test chamber to be provided with a test gas with variable test parameters;

a control circuit connected to said exhaust probe;

a test control computer for setting and monitoring the variable test parameters in said test chamber; and a data line, said control circuit and said test control computer communicating with one another via said data line.

14. The device according to claim 13, wherein:

said control circuit has a serial interface; and said serial interface connects said data line to said control circuit.

15. The device according to claim 13, wherein said exhaust probe is a motor vehicle exhaust probe.

16. The device according to claim 13, wherein:

said exhaust probe operates according a principle of a galvanic oxygen concentration cell with a solid electrolyte, and said exhaust probe acquires measured values under given test conditions; and said control circuit controls pump currents for said exhaust probe, and said control circuit stores the measured values as one of correction values and test values.

17. The device according to claim 16, wherein said control circuit corrects the pump currents based on the measured values.

* * * * *